(12) United States Patent
Nöcker et al.

(10) Patent No.: US 10,973,747 B2
(45) Date of Patent: Apr. 13, 2021

(54) METHOD FOR COLOURING KERATIN FIBERS

(71) Applicant: KAO GERMANY GMBH, Darmstadt Hessen (DE)

(72) Inventors: Bernd Nöcker, Darmstadt (DE); Anne Neu, Darmstadt (DE); Fariba Ghiasi, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 15 days.

(21) Appl. No.: 16/473,102

(22) PCT Filed: Dec. 21, 2017

(86) PCT No.: PCT/EP2017/084045
§ 371 (c)(1),
(2) Date: Jun. 24, 2019

(87) PCT Pub. No.: WO2018/122090
PCT Pub. Date: Jul. 5, 2018

(65) Prior Publication Data
US 2020/0188262 A1    Jun. 18, 2020

(30) Foreign Application Priority Data

Dec. 27, 2016  (EP) ..................... 16206991

(51) Int. Cl.
| | |
|---|---|
| *A61Q 5/10* | (2006.01) |
| *A61K 8/46* | (2006.01) |
| *A61K 8/19* | (2006.01) |
| *A61K 8/22* | (2006.01) |
| *A61K 8/34* | (2006.01) |
| *A61K 8/41* | (2006.01) |
| *A61K 8/44* | (2006.01) |
| *A61K 8/73* | (2006.01) |
| *A61K 8/81* | (2006.01) |
| *A61K 8/891* | (2006.01) |
| *A45D 7/00* | (2006.01) |

(52) U.S. Cl.
CPC .................. *A61K 8/46* (2013.01); *A61K 8/19* (2013.01); *A61K 8/22* (2013.01); *A61K 8/342* (2013.01); *A61K 8/347* (2013.01); *A61K 8/41* (2013.01); *A61K 8/415* (2013.01); *A61K 8/418* (2013.01); *A61K 8/44* (2013.01); *A61K 8/463* (2013.01); *A61K 8/73* (2013.01); *A61K 8/731* (2013.01); *A61K 8/8141* (2013.01); *A61K 8/891* (2013.01); *A45D 2007/001* (2013.01); *A61K 2800/432* (2013.01); *A61K 2800/48* (2013.01)

(58) Field of Classification Search
CPC . A61Q 5/065; A61Q 5/06; A61Q 5/10; A61K 8/46; A61K 8/41; A45D 2007/001
USPC ............................... 8/405; 132/208
See application file for complete search history.

(56) References Cited

U.S. PATENT DOCUMENTS

| | | | |
|---|---|---|---|
| 2014/0150185 A1* | 6/2014 | Lalleman | A61K 8/447 8/405 |
| 2015/0231050 A1 | 8/2015 | Lan et al. | |
| 2018/0078478 A1* | 3/2018 | Murphy | C09B 29/3665 |

FOREIGN PATENT DOCUMENTS

| | | |
|---|---|---|
| EP | 1 302 195 A1 | 4/2003 |
| EP | 1 428 497 A1 | 6/2004 |
| EP | 2 020 252 A1 | 2/2009 |
| FR | 2 978 039 A1 | 1/2013 |
| GB | 2 497 886 A | 6/2013 |
| JP | 2010-235572 A | 10/2010 |
| WO | 2010/032034 A2 | 3/2010 |
| WO | 2013/011116 A2 | 1/2013 |
| WO | 2015/086269 A1 | 6/2015 |
| WO | 2016/166201 A1 | 10/2016 |

OTHER PUBLICATIONS

International Search Report dated Jan. 19, 2018, corresponds to International Application No. PCT/EP2017/084045.

* cited by examiner

*Primary Examiner* — Eisa B Elhilo
(74) *Attorney, Agent, or Firm* — Norris McLaughlin, P.A.

(57) ABSTRACT

The present invention relates to a method of coloring keratin fibers, especially human hair, which delivers intensive, long lasting, brilliant colors and provides improved grey coverage. Kit therefore is disclosed as well. The method of colouring hair involves treating hair prior to colouring with an alkaline reducing agent.

16 Claims, No Drawings

METHOD FOR COLOURING KERATIN FIBERS

This application is the U.S. National Stage of International Application No. PCT/EP2017/084045, filed Dec. 21, 2017, which claims foreign priority benefit under 35 U.S.C. § 119 of European Application No. 16206991.8 filed Dec. 27, 2016 the disclosures of which are incorporated herein by reference.

The present invention relates to a method of coloring keratin fibers, especially human hair, which delivers intensive, long lasting, brilliant colors and provides improved grey coverage. Kit therefore is disclosed as well.

Hair dyeing has been practiced for many decades, on one hand in order to refresh the hair color, and on the other hand to color grey hair so that the hair has homogeneous color. In hair dressing practice, obtaining intensive coloration and grey coverage are aimed at and at the same time the color thus obtained should also last longer so that the customers may wear the color for a long time without loss of hair beauty.

Another problem occurs during hair coloring is that the damage of hair. Especially the oxidative process does result in hair damage if used in excessive amounts and also unnecessarily repeatedly. In other words, achieving long lasting hair colors will reduce coloring frequency and therefore hair will not be excessively stressed and damaged.

The inventors of the present invention paid attention to arrive at a novel method for coloring keratin fibers, especially human hair, for achieving intensive, long lasting colours with improved grey coverage and less damaging to hair. At the same time, it has been observed that hair comprising parts with various degree of damage is also colored homogeneously from root to tip.

The inventors have unexpectedly found out that treating hair prior to application of hair coloring composition onto hair with an alkaline composition comprising reducing agent results in intensive and long lasting colors. At the same time, it has been observed that the hair with grey parts is colored homogeneously without leaving any grey hair and hair thus colored is damaged in a lesser extent than the hair colored without using the reductive step.

Hair dyeing in the presence of reducing agent has been disclosed in WO 2010/032034 A2. The document discloses mixing the reducing composition and hair dye comprising composition prior to application onto hair in order to dye hair intensively. The document is silent on separate applications of the reducing and dyeing composition onto hair.

Pretreating hair prior to hair dyeing is known form EP1428497, JP2010-235572 and EP 1302195. The documents do disclose various compositions to be applied prior to coloring hair but none of the publications relate to treating hair with reducing composition prior to hair coloring.

Accordingly, the first object of the present invention is a method for coloring keratin fibers, especially human hair, comprising the following steps a—applying a Composition A onto hair which is an alkaline aqueous composition comprising one or more reducing agent and leaving it on the hair for a period of 1 to 30 min, preferably 1 to 15 min, more preferably 1 to 10 min and the most preferably 1 to 5 min, b—rinsing off the hair with water and towel drying, c—applying a Composition B onto hair which is an aqueous composition comprising one or more hair dyes and leaving it on the hair for a period of 1 to 45 min at a temperature 20 to 45° C., d—rinsing off the hair with water, e—optionally, washing hair with a cleansing composition or treating the hair with an aqueous composition comprising hydrogen peroxide at a concentration 0.1 to 3%, preferably 0.1 to 2% and more preferably 0.2 to 1% by weight calculated to the total of the aqueous composition for a period 1 to 10 min, preferably 1 to 5 min and more preferably 1 to 2 min and rinsing off the aqueous composition, f—towel drying and drying the hair.

The second object is the use of reductive treatment to achieve intensive coloration of keratin fibers, especially human hair, when hair is treated subsequently with an aqueous composition comprising one or more hair dyes.

The third object is the use of reductive treatment to achieve long lasting coloration of keratin fibers, especially human hair, when hair is treated subsequently with an aqueous composition comprising one or more hair dyes.

The fourth object is the use of reductive treatment to reduce damage of keratin fibers, especially human hair, during a subsequent coloration with an aqueous composition comprising one or more hair dyes.

The fifth object is the use of reductive treatment to color keratin fibers, especially human hair, comprising parts with various degree of damage homogeneously during a subsequent coloration with an aqueous composition comprising one or more hair dyes.

The sixth object is a kit for hair comprising an alkaline aqueous composition comprising one or more reducing agent and an aqueous composition comprising one or more hair dyes.

The Composition A used in the method of the present invention is an alkaline composition and comprises one or more alkalizing agents selected from the compounds according to general structure $$R_4R_6R_6N$$

wherein $R_4$, $R_5$ and $R_6$ are same or different H, $C_1$ to $C_4$ alkyl, $C_3$ to $C_4$ unsaturated alkyl, $C_3$ to $C_4$ branched alkyl, $C_1$ to $C_4$ hydroxy alkyl, $C_3$ to $C_4$ unsaturated hydroxy alkyl and $C_3$ to $C_4$ branched hydroxy alkyl.

The Composition B used in the method of the present invention comprises one or more alkalizing agents preferably selected from the compounds according to general structure $$R_4R_5R_6N$$

wherein $R_4$, $R_5$ and $R_6$ are same or different H, $C_1$ to $C_4$ alkyl, $C_3$ to $C_4$ unsaturated alkyl, $C_3$ to $C_4$ branched alkyl, $C_1$ to $C_4$ hydroxy alkyl, $C_3$ to $C_4$ unsaturated hydroxy alkyl and $C_3$ to $C_4$ branched hydroxy alkyl.

Suitable alkalizing agents are ammonia, monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, aminomethyl propanol and diethanolbutylamine. Preferred alkalizing agents are ammonia, monoethanolamine and aminomethyl propanol. The most preferred is aminomethyl propanol abbreviated as AMP.

The alkalizing agent is comprised in the Composition A at a total concentration of 0.25 to 10%, preferably 0.5 to 7.5%, more preferably 0.5 to 6% and most preferably 0.75 to 5% by weight calculated to the total of the Composition A.

The alkalizing agent is comprised in the Composition B at a total concentration of 0.25 to 10%, preferably 0.5 to 7.5%, more preferably 0.5 to 6% and most preferably 0.75 to 5% by weight calculated to the total of the Composition B.

The Composition A comprises one or more reducing agents. Useful are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts and sodium sulfite. Preferred are thioglycolic acid and/or its salts, thiolactic acid and/or its salts, and cysteine or its derivatives and/or its salts. The most preferred is thioglycolic acid and/or its salts.

One or more reducing agents are comprised in the composition A at a total concentration in the range of 0.1 to 5%, preferably 0.2 to 4%, more preferably 0.25 to 3%, most preferably 0.25 to 2.5% and in particular 0.25 to less than 2.0% by weight calculated to the total of the Composition A.

The pH of the composition A is in the range of 8 to 11, preferably 8 to 10 and more preferably 8.5 to 9.5.

The Composition B is an aqueous composition and comprises one or more hair dyes selected from hair direct dyes and oxidative dyestuff precursors. The hair direct dyes are selected from anionic, cationic and neutral dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Blue 18, HC Red 18 and HC yellow 16 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18 and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31 and HC Blue 17. The most preferred ones are Basic Red 51, Basic Yellow 87 and Basic Orange 31 sold by BASF, and HC Blue 17.

Suitable neutral nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The Composition B comprises one or more hair direct dye at a total concentration in the range of 0.01 to 10%, preferably 0.05 to 7.5% and more preferably 0.1 to 5% by weight calculated to the total of the Composition B. The composition may also comprise mixtures of several direct dyes i.e. an anionic, a cationic and/or a nonionic ones. In such a case the dyes may be mixed at any ratio with each other.

The Composition B comprises one or more oxidative dye precursors and optionally one or more coupling substances.

Suitable non-limiting examples of oxidative dye precursor classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and substituted derivatives, and naphthols.

Non-limiting examples of the oxidative dye precursor compounds are p-phenylenediamine, p-aminophenol, 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene, 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof, and mixture thereof.

The total concentration of the dye precursors (developing substances) ranges between 0.001 to 5%, preferably 0.01 to 4% and more preferably 0.05 to 3%, and most preferably 0.1 to 2% by weight, calculated to the total of the composition A.

The suitable non-limiting examples of the coupling substance if present in the composition A are 5-amino-2- methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl) amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof and mixture thereof.

In the composition B, the coupling substance(s) as reaction partners of the developing substance(s) are present in approximately the same molecular proportions as the developing substances, i.e. at a total concentration in the range of 0.001 to 5%, preferably 0.01 to 4% and more preferably 0.05 to 3%, and most preferably 0.1 to 2% by weight, calculated to the total of the composition B.

It should be noted that the composition B may comprise mixture of oxidative dye precursor and hair direct dyes.

The total dyestuff concentration in the composition B is in the range of 0.001 to 15%, preferably 0.01 to 12.5% and more preferably 0.05 to 10% by weight, calculated to the total of the Composition B.

The composition B can comprise one or more oxidizing agent(s). The oxidizing agents suitable are hydrogen peroxide, urea peroxide, melamin peroxide or perborate salts. The most preferred is hydrogen peroxide. The composition B comprises one or more oxidizing agents at a total concentration of 1 to 20% by weight, preferably 2 to 15%, more preferably 2 to 12% and most preferably 3 to 12% by weight, calculated to total of composition B.

In a preferred embodiment of the present invention, the oxidizing agent is added into the Composition B prior to application of the composition onto hair.

The pH of the composition B is in the range of 2 to 11.

The compositions A and/or B used in the method of the present invention comprises one or more ingredients selected from the following ingredients or classes of ingredients
    one or more surfactants selected from anionic, non-ionic, cationic or amphoteric surfactants,
    one or more fatty alcohol,
    one or more thickening polymers,
    sequestering agents,
    fragrance,
    fatty acids,
    preservatives,
    organic solvents, and
    silicones.

Compositions A and/or B according to the present invention may comprise surfactants selected from anionic, non-ionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principal known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are 08-020-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants suitable are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "PluronicsR", as well as fatty alcohol ethoxylates, 022-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Suitable cationic surfactants are according to the general structure $$R_6-\overset{R_9}{\underset{R_5}{N^+}}-R_4 \quad X^-$$

where $R_5$ is a saturated or unsaturated, branched or linear alkyl chain with 8-22 C atoms or $$R_7CONH(CH_2)_n$$

where $R_7$ is saturated or unsaturated, branched or linear alkyl chain with 7-21 C atoms and n has typical value of 1-4 or $$R_8COO(CH_2)_n$$

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or $$R_7CONH(CH_2)_n$$

or $$R_8COO(CH_2)_n$$

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The total concentration of one or more surfactants in the compositions A and/or B is in the range of 0.1 to 20%, preferably 0.2 to 15% and most preferably 0.2-10% by weight, calculated to the total of the Composition A or B.

The compositions A and/or B may comprise one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, oleyl alcohol, octyldodecanol, behenyl alcohol and cetostearyl alcohol.

The total concentration of fatty alcohol is in the range from 0.5 to 20%, preferably 1 to 15% by weight, calculated to total of the Composition A or B.

In a further preferred embodiment of the present invention, the Composition A and/or B comprises one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 minute, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickeners Carbomer and its derivatives. The particularly preferred thickening agent is dehydroxanthan gum. The thickening agents are preferably comprised in the composition B at a total concentration in the range of 0.1 to 5%, preferably, 0.2 to 3%, more preferably 0.25 to 2.5% and most preferably 0.3 to 2% by weight calculated to the total of the composition B.

The compositions A and/or B may comprise one or more ceramide compound, such as the one according to general formula $$R_{11}-O-CH_2$$
$$|$$
$$CHOH$$
$$|$$
$$R_{12}-\underset{\underset{O}{\|}}{C}-\underset{\underset{R_{13}}{|}}{N}-CH_2$$

where $R_{11}$ and $R_{12}$ are independent from each other an alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% by weight calculated to total or each composition.

The compositions A and/or B may comprise ubiquinone of the formula:

[Structure of ubiquinone with H$_3$CO groups, CH$_3$ groups, and isoprenoid side chain with n repeating units]

wherein n is a number from 1 to 10. Concentration of ubiquinone can vary between 0.001% and 10% by weight, calculated to the total of each composition.

The compositions A and/or B may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1 to 15%, preferably 0.5 to 12.5% and more preferably 1 to 10% and most preferably 1 to 7.5% by weight calculated to the total of each composition.

The compositions A and/or B may comprise one or more of the compounds selected from sequestering agents, fragrances, preservatives, silicones.

The following examples are to illustrate the invention but not to limit it.

EXAMPLE 1

| Composition A | |
|---|---|
| | % by weight |
| Cetearyl alcohol | 10 |
| Oleyl alcohol | 5 |
| Ammonia | 1.3 |
| Thioglycolic acid | 1.7 |
| Ceteareth-20 | 1.0 |
| EDTA | 0.5 |
| Fragrance | 0.5 |
| Water | to 100 | pH of the above composition is 10.0.

| Composition B | |
|---|---|
| | % by weight |
| Carbomer | 1.5 |
| Mineral oil | 3 |
| Benzyl alcohol | 4.3 |
| PEG-40 hydrogenated castor oil | 2 |
| HC Yellow 10 | 0.1 |
| HC Yellow 16 | 0.1 |
| HC Blue 18 | 0.1 |
| HC Red 18 | 0.1 |
| EDTA | 0.5 |
| Fragrance | 0.5 |
| Water | to 100 |

The human hair was applied the Composition A and left on the hair for 5 min and rinsed off from hair. Subsequently, the Composition B was applied and left on the hair from 30 min at ambient temperature and rinsed off from hair and the hair was shampooed and towel dried and dried with a hair drier.

For comparative purposes another hair streak was applied water and left on the hair for 5 min and afterwards rinsed off and subsequently, the Composition B was applied and left on the hair from 30 min and rinsed off from hair and the hair was shampooed and towel dried and dried with a hair drier.

Hair colour was measured with a laboratory colorimeter as L, a and b values. And the color difference to the color of the hair prior to coloration was calculated with the following equation.

$$\Delta E = SQRT(\Delta L^2 + \Delta a^2 + \Delta b^2)$$

The following results were observed.

| | L | a | b | ΔE |
|---|---|---|---|---|
| With pre-treatment | 23 | 4.4 | 7.2 | 60.2 |
| Without pre-treatment | 33.6 | 6.8 | 15.9 | 49.5 |

From the above results it is beyond any doubt that treating hair with the reducing composition resulted in intensive colouration of the hair (the lower the L value, the darker the colour) and larger colour difference was observed as expressed with higher ΔE value.

In a parallel application after rinsing of the dyeing composition B from the hair, hair was treated with a composition comprising 1% by weight hydrogen peroxide and after rinsing off the hydrogen peroxide composition from the hair with water, hair was towel dried and dried with a hair drier. The above results were confirmed as well using the alternative process.

EXAMPLE 2

| Composition A | |
|---|---|
| | % by weight |
| Cetearyl alcohol | 10 |
| Oleyl alcohol | 5 |
| Aminomethylpropanol | 3.2 |
| Thioglycolic acid | 1.7 |
| Ceteareth-20 | 1.0 |
| Hydroxyethylcellulose | 0.5 |
| EDTA | 0.5 |
| Fragrance | 0.5 |
| Water | to 100 | pH of the above composition is 9.9.

| Composition B | |
|---|---|
| | % by weight |
| Cetearyl alcohol | 10 |
| Oleth-5 | 4 |
| Oleic acid | 5 |
| Sodium cetearyl sulfate | 1.3 |
| Sodium lauryl sulphate | 2 |
| Ammonium hydroxide | 5 |
| p-toluene diamine sulfate | 0.8 |
| Resorcinol | 0.3 |
| m-aminophenol | 0.1 |
| 4-amino-2-hydroxytoluene | 0.1 |
| EDTA | 0.5 |
| Fragrance | 0.5 |
| Water | to 100 |

The human hair was applied the Composition A and left on the hair for 4 min and rinsed off from hair. Subsequently, the Composition B was applied after mixing with an oxidizing composition comprising 6% by weight hydrogen peroxide at a weight ratio of 1:1, and left on the hair from 30 min at ambient temperature and rinsed off from hair and the hair was shampooed and towel dried and dried with a hair drier.

For comparative purposes another hair streak was applied water and left on the hair for 4 min and afterwards rinsed off and subsequently, the Composition B was applied after mixing with an oxidizing composition comprising 6% by weight hydrogen peroxide at a weight ratio of 1:1, and left on the hair from 30 min at ambient temperature and rinsed off from hair and the hair was shampooed and towel dried and dried with a hair drier.

Hair colour was measured and analysed as in Example 1. The following results were observed.

| | L | a | b | ΔE |
|---|---|---|---|---|
| With pre-treatment | 34 | 4.6 | 11 | 48.7 |
| Without pre-treatment | 36 | 5.2 | 13.4 | 46.1 |

From the above results it is clear that treating hair with the reducing composition resulted in intensive colouration of the hair (the lower the L value, the darker the colour) and larger colour difference was observed as expressed with higher ΔE value.

EXAMPLE 3

Composition A

|  | % by weight |
|---|---|
| Cetearyl alcohol | 10 |
| Oleyl alcohol | 5 |
| Ammonia | 1.3 |
| Thioglycolic acid | 1.7 |
| Ceteareth-20 | 1.0 |
| EDTA | 0.5 |
| Fragrance | 0.5 |
| Water | to 100 | pH of the above composition is 10.0.

Composition B

|  | % by weight |
|---|---|
| Xanthan gum | 2.5 |
| PEG-9-Dimethicone | 2 |
| Propylene Carbonate | 20 |
| Alcohol | 10 |
| Lactic acid | 5 |
| Acid violet 43 | 0.25 |
| Acid orange 7 | 0.2 |
| Acid Yellow 3 | 0.1 |
| EDTA | 0.5 |
| Fragrance | 0.5 |
| Water | to 100 |

The human hair was applied the Composition A and left on the hair for 5 min and rinsed off from hair. Subsequently, the Composition B was applied and left on the hair from 30 min and rinsed off from hair and the hair was shampooed and towel dried and dried with a hair drier.

For comparative purposes another hair streak was applied water and left on the hair for 5 min and afterwards rinsed off and subsequently, the Composition B was applied and left on the hair from 30 min and rinsed off from hair and the hair was shampooed and towel dried and dried with a hair drier.

Hair colour was measured with a laboratory colorimeter as L, a and b values. And the color difference to the color of the hair prior to coloration was calculated with equation given under Example 1.

The following results were observed.

|  | L | a | b | DE |
|---|---|---|---|---|
| With pre-treatment | 22 | 9.2 | 12 | 61.2 |
| Without pre-treatment | 30.6 | 8.6 | 10.4 | 52.8 |

From the above results it is beyond any doubt that treating hair with the reducing composition resulted in intensive colouration of the hair (the lower the L value, the darker the colour) and larger colour difference was observed as expressed with higher DE value.

EXAMPLE 4

Composition A

|  | % by weight |
|---|---|
| Cetearyl alcohol | 10 |
| Oleyl alcohol | 5 |
| Monoethanolamine | 4.6 |
| Thioglycolic acid | 1.7 |
| Cetrimonium chloride | 1.0 |
| EDTA | 0.5 |
| Fragrance | 0.5 |
| Water | to 100 | pH of the above composition is 10.0.

Composition B

|  | % by weight |
|---|---|
| Cetearyl alcohol | 2 |
| Behentrimonium chloride | 1 |
| Phenoxyethanol | 2 |
| Basic yellow 57 | 1 |
| HC blue 11 | 0.5 |
| EDTA | 0.5 |
| Fragrance | 0.5 |
| Water | to 100 |

The human hair was applied the Composition A and left on the hair for 3 min and rinsed off from hair. Subsequently, the Composition B was applied and left on the hair from 30 min and rinsed off from hair and the hair was shampooed and towel dried and dried with a hair drier.

For comparative purposes another hair streak was applied water and left on the hair for 5 min and afterwards rinsed off and subsequently, the Composition B was applied and left on the hair from 30 min and rinsed off from hair and the hair was shampooed and towel dried and dried with a hair drier.

Hair colour was measured with a laboratory colorimeter as L, a and b values. And the color difference to the color of the hair prior to coloration was calculated as in example 1.

The following results were observed.

|  | L | a | b | DE |
|---|---|---|---|---|
| With pre-treatment | 44 | −2 | 21 | 39.4 |
| Without pre-treatment | 61 | −2 | 23 | 23.8 |

From the above results it is beyond any doubt that treating hair with the reducing composition resulted in intensive colouration of the hair (the lower the L value, the darker the colour) and larger colour difference was observed as expressed with higher ΔE value.

Similar results were observed as in the Examples 1 to 4 with the following hair colouring compositions when used in combination with the Compositions A of the Examples 1 to 4 and according to the process as described under each of the Examples 1 to 4.

EXAMPLE 5

| Composition B | |
|---|---|
| | % by weight |
| Carbomer | 1.5 |
| Mineral oil | 3 |
| Benzyl alcohol | 4.3 |
| Alcohol | 2 |
| Sodium lauryl sulphate | 2 |
| Acid Yellow 3 | 0.1 |
| HC Yellow 16 | 0.1 |
| HC Blue 18 | 0.05 |
| HC Red 18 | 0.02 |
| Acid red 52 | 0.02 |
| EDTA | 0.5 |
| Fragrance | 0.5 |
| Water | to 100 |

EXAMPLE 6

| Composition B | |
|---|---|
| | % by weight |
| Xanthan gum | 1 |
| Dimethicone | 2 |
| Benzyl alcohol | 4.3 |
| Phenoxyethanol | 2 |
| Sodium cetearyl sulphate | 2 |
| Acid Yellow 3 | 0.1 |
| HC Yellow 16 | 0.15 |
| HC Blue 18 | 0.02 |
| HC Red 18 | 0.08 |
| Acid red 52 | 0.075 |
| EDTA | 0.5 |
| Fragrance | 0.5 |
| Water | to 100 |

EXAMPLE 7

| Composition B | |
|---|---|
| | % by weight |
| Carbomer | 1 |
| Dimethicone | 0.25 |
| Mineral oil | 1 |
| Phenoxyethanol | 2 |
| Sodium cetearyl sulphate | 2 |
| Acid Yellow 3 | 0.1 |
| HC Yellow 16 | 0.15 |
| HC Blue 18 | 0.02 |
| HC Red 18 | 0.08 |
| Acid red 52 | 0.075 |
| EDTA | 0.5 |
| Fragrance | 0.5 |
| Water | to 100 |

EXAMPLE 8

| Composition B | |
|---|---|
| | % by weight |
| Cetearyl alcohol | 5 |
| Dimethicone | 0.25 |
| Mineral oil | 1 |
| Phenoxyethanol | 2 |
| Ceteareth-20 | 2 |
| Acid Yellow 3 | 0.1 |
| HC Yellow 16 | 0.15 |
| HC Blue 18 | 0.1 |
| HC Red 18 | 0.08 |
| Acid red 52 | 0.1 |
| EDTA | 0.5 |
| Fragrance | 0.5 |
| Water | to 100 |

EXAMPLE 9

| Composition B | |
|---|---|
| | % by weight |
| Carbomer | 1 |
| Cetearyl alcohol | 4 |
| Dimethicone | 0.25 |
| Mineral oil | 1 |
| Phenoxyethanol | 2 |
| Ceteareth-20 | 2 |
| Acid Yellow 3 | 0.1 |
| HC Yellow 16 | 0.15 |
| HC Blue 18 | 0.1 |
| HC Red 18 | 0.08 |
| Acid red 52 | 0.1 |
| EDTA | 0.5 |
| Fragrance | 0.5 |
| Water | to 100 |

The invention claimed is:

1. A method for coloring keratin fibers, the method comprising:
    a—applying Composition A onto hair and leaving the Composition A on the hair for a period of 1 minute to 30 minutes, wherein the Composition A is an alkaline aqueous composition having a pH in the range of 8 to 10 and comprising one or more reducing agents and one or more alkalizing agents selected from the compounds according to general structure $R_4R_5R_6N$ wherein R4, R5 and R6 are same or different H, C1 to C4 alkyl, C3 to C4 unsaturated alkyl, C3 to C4 branched alkyl, C1 to C4 hydroxy alkyl, C3 to C4 unsaturated hydroxy alkyl, and C3 to C4 branched hydroxy alkyl, present at a total concentration of 0.25 to 10%, by weight calculated to a total of the Composition A;
    b—rinsing the Composition A off the hair with water and towel drying;
    c—applying Composition B onto the rinsed hair and leaving the Composition B on the rinsed hair for a period of 1 minute to 45 minutes at a temperature from 20 to 45° C., the Composition B is an aqueous composition comprising one or more hair dyes;
    d—rinsing the Composition B off the rinsed hair with water;

g—optionally, washing the twice rinsed hair with a cleansing composition or treating the twice rinsed hair with an aqueous composition comprising hydrogen peroxide at a concentration 0.1 to 3%, by weight calculated to a total of the aqueous composition for a period of 1 minute to 10 minutes, and rinsing the aqueous composition off the twice rinsed hair; and e—towel drying and drying the thrice rinsed hair.

2. The method of claim 1, wherein the Composition A has a pH in the range of 8 to 9.9.

3. The method of claim 1, wherein the one or more reducing agents is selected from thiogylcolic acid and/or its salts, cysteamine and/or its salts, thioglycerin and/or its salts, glycerin esters of thioglycolic acid and/or its salts, thiolactic acid and/or its salts, cysteine and/or its salts and sodium sulfite.

4. The method of claim 1, wherein the one or more reducing agents is selected from thioglycolic acid and/or its salts.

5. The method of claim 1, wherein the one or more hair dyes is selected from hair direct dyes and oxidative dyestuff precursors.

6. The method of claim 5, wherein the hair direct dyes are selected from one or more anionic direct dyes, one or more cationic dyes, and one or more neutral nitro dyes.

7. The method of claim 6, wherein the one or more anionic direct dyes is selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Blue 18, HC Red 18, HC yellow 16, and their alkali metal salts.

8. The method of claim 6, wherein the one or more cationic dyes is selected from Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, Basic Orange 31, and HC Blue 17.

9. The method of claim 6, wherein the one or more neutral nitro dyes is selected from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol, and 2-hydroxyethylpicramic acid.

10. The method of claim 1, wherein the one or more hair dyes is selected from HC Yellow 16, HC Blue 18 and HC Red 18.

11. The method of claim 1, wherein the Composition B has a pH in the range of 2 to 11.

12. The method of claim 1, wherein the composition B further comprises one or more alkalizing agents selected from compounds according to general structure

R4R5R6N wherein R4, R5 and R6 are same or different H, C1 to C4 alkyl, C3 to C4 unsaturated alkyl, C3 to C4 branched alkyl, C1 to C4 hydroxy alkyl, C3 to C4 unsaturated hydroxy alkyl and C3 to C4 branched hydroxy alkyl, at a total concentration of 0.25 to 10%, by weight calculated to a total of the Compositions B.

13. The method of claim 1, wherein the one or more alkalizing agents of the Composition A is selected from ammonia, monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, aminomethyl propanol, and diethanolbutylamine.

14. The method of claim 1, wherein Composition B further comprises one or more oxidizing agent present at a concentration in the range of 1 to 12% by weight, calculated to a total weight of the Composition B.

15. The method of claim 1, wherein at least one of the Composition A and the Composition B further comprises:
one or more surfactants;
one or more fatty alcohols;
one or more thickening polymers;
one or more sequestering agents;
one or more fragrances;
one or more fatty acids;
one or more preservatives;
one or more organic solvents; and
one or more silicones.

16. The method of claim 1, wherein the Composition A has a pH in the range of 8 to 9.9.

* * * * *